United States Patent
Conroy et al.

(10) Patent No.: US 10,351,789 B2
(45) Date of Patent: Jul. 16, 2019

(54) METHOD OF IMPROVING THE ACCURACY WHEN QUANTIFYING FLUORESCENCE MARKERS IN FUELS

(71) Applicant: Authentix, Inc., Addison, TX (US)

(72) Inventors: Jeffrey L. Conroy, Allen, TX (US); Philip B. Forshee, McKinney, TX (US)

(73) Assignee: Authentix, Inc., Addison, TX (US)

( * ) Notice: Subject to any disclaimer, the term of this patent is extended or adjusted under 35 U.S.C. 154(b) by 155 days.

(21) Appl. No.: 15/632,532

(22) Filed: Jun. 26, 2017

(65) Prior Publication Data
US 2018/0371342 A1    Dec. 27, 2018

(51) Int. Cl.
| | | |
|---|---|---|
| *C10L 1/00* | (2006.01) | |
| *C10L 1/16* | (2006.01) | |
| *G01N 21/64* | (2006.01) | |
| *G01N 21/77* | (2006.01) | |
| *G01N 33/22* | (2006.01) | |
| *G01N 33/28* | (2006.01) | |
| C10L 1/182 | (2006.01) | |
| C10L 1/20 | (2006.01) | |
| G01N 30/02 | (2006.01) | |
| H01J 49/26 | (2006.01) | |
| G01N 21/33 | (2006.01) | |
| G01N 21/3504 | (2014.01) | |

(52) U.S. Cl.
CPC ............ *C10L 1/003* (2013.01); *C10L 1/1633* (2013.01); *G01N 21/643* (2013.01); *G01N 21/77* (2013.01); *G01N 33/28* (2013.01); *C10L 1/16* (2013.01); *C10L 1/1822* (2013.01); *C10L 1/202* (2013.01); *G01N 21/33* (2013.01); *G01N 21/3504* (2013.01); *G01N 33/22* (2013.01); *G01N 33/2882* (2013.01); *G01N 2021/7786* (2013.01); *G01N 2030/025* (2013.01); *G01N 2030/027* (2013.01); *H01J 49/26* (2013.01); *Y10T 436/21* (2015.01)

(58) Field of Classification Search
CPC .......... C10L 1/003; C10L 1/16; C10L 1/1633; C10L 1/1822; C10L 1/202; G01N 2030/025; G01N 2030/027; G01N 21/33; G01N 21/3504; G01N 21/6458; G01N 30/72; G01N 30/7206; G01N 33/22; G01N 33/28; G01N 33/2882; G01N 21/643; G01N 21/77; H01J 49/26; Y10T 436/21; Y10T 436/212; Y10T 436/214; Y10T 436/19; Y10T 436/24; Y10T 436/25625
USPC ......... 436/60, 139, 140, 141, 124, 161, 164, 436/172, 173, 179; 422/82.05, 82.08, 89
See application file for complete search history.

(56) References Cited

U.S. PATENT DOCUMENTS

| | | | | |
|---|---|---|---|---|
| 8,129,190 | B2* | 3/2012 | Forshee | C10L 1/003 208/15 |
| 8,592,213 | B2* | 11/2013 | Wilkinson | G01N 21/3577 436/27 |
| 9,097,669 | B2* | 8/2015 | Webster | G01N 21/643 |
| 9,222,043 | B2* | 12/2015 | Forshee | C10L 1/003 |
| 9,366,661 | B1 | 6/2016 | Conroy et al. | |
| 2008/0118982 | A1* | 5/2008 | Forshee | C10L 1/003 436/56 |
| 2011/0020940 | A1* | 1/2011 | Knapton | C10L 1/003 436/60 |
| 2013/0179090 | A1* | 7/2013 | Conroy | G01N 21/643 702/25 |
| 2017/0306255 | A1* | 10/2017 | Conroy | C07C 323/20 |

\* cited by examiner

*Primary Examiner* — Maureen Wallenhorst
(74) *Attorney, Agent, or Firm* — Conley Rose, P.C.; Rodney B. Carroll

(57) ABSTRACT

A method of increasing the accuracy of the quantification of an analyte in a hydrocarbon, the analyte containing a marking compound, by obtaining a first sample containing (a) the hydrocarbon and (b) the marking compound, obtaining a homogeneity inducing material, contacting the homogeneity inducing material with an aliquot of the first sample in a volumetric ratio of greater than or equal to about 5:1 to produce a second sample, and determining an amount of the marking compound in the second sample using an analytical technique based on the marking material.

20 Claims, 2 Drawing Sheets

METHOD OF IMPROVING THE ACCURACY WHEN QUANTIFYING FLUORESCENCE MARKERS IN FUELS

TECHNICAL FIELD

The present disclosure relates to quantifying marking compounds in hydrocarbon samples; more particularly, the present disclosure relates to methods to improve accuracy when quantifying marking compounds in hydrocarbon samples; still more particularly, this disclosure relates to methods of improving the accuracy when quantifying marking compounds in hydrocarbon samples by combining the samples with a matrix, thus increasing the degree of homogeneity.

BACKGROUND

Marking compounds, such as fluorescence markers, are routinely utilized to mark hydrocarbons, such as fuels. When such marking compounds are utilized in hydrocarbons of varying composition, the marking compounds can sometimes undesirably exhibit variable response (i.e., variable intensity) without any noticeable changes to analytical results, such as spectral shape or wavelength. In such instances, standard chemometric models may not adequately handle quantification of the marking compounds.

Accordingly, there exists an ongoing need for methods of improving the accuracy when quantifying marker compounds, such as fluorescence markers, in hydrocarbons, such as fuels, as will be described in more detail hereinbelow.

SUMMARY

Herein disclosed is a method of increasing accuracy of the quantification of an analyte in a hydrocarbon, the analyte comprising a marking compound, the method comprising: obtaining a first sample comprising (a) the hydrocarbon and (b) the marking compound; obtaining a homogeneity inducing material; contacting the homogeneity inducing material with an aliquot of the first sample in a volumetric ratio of greater than or equal to about 5:1 to produce a second sample; and determining an amount of the marking compound in the second sample using an analytical technique based on the marking material.

Also disclosed herein is a method of increasing agreement between at least two differing and independent analytical techniques, the method comprising: obtaining a first sample comprising (a) a hydrocarbon, (b) a marking compound, and (c) a homogeneity-varying material, wherein the first sample has a degree of homogeneity in the range of from about 0.1 to about 0.4; contacting a matrix with an aliquot of the first sample in a volumetric ratio of greater than or equal to about 5:1 to produce a second sample, wherein the second sample has a degree of homogeneity in the range of from about 0.8 to about 0.95; determining an amount of the marking compound in the first sample using a first of the least two differing and independent analytical techniques; and determining an amount of the marking compound in the second sample using a second of the least two differing and independent analytical techniques.

Further disclosed herein is a method of increasing agreement between at least two differing and independent analytical techniques, the method comprising: obtaining a fuel comprising (a) a fluorescent marking compound and (b) a signal-dampening material, wherein the fuel has a degree of homogeneity in the range of from about 0.1 to about 0.2; contacting a matrix with an aliquot of the fuel in a volumetric ratio of greater than or equal to about 5:1 to produce a sample, wherein the sample has a degree of homogeneity of greater than or equal to about 0.8; and determining a concentration of the fluorescent marking compound in the sample using a first of the at least two differing and independent analytical techniques.

Also disclosed herein is a method of increasing agreement between at least two differing and independent analytical techniques, the method comprising: obtaining a first sample comprising (a) a hydrocarbon, (b) a marking compound producing a signal in response to a stimulus, and (c) at least one signal-dampening material; determining an amount of the marking compound in the first sample using a first of the at least two differing and independent analytical techniques; contacting a matrix with an aliquot of the first sample in a volumetric ratio of greater than or equal to about 5:1 to produce a second sample; and determining an amount of the marking compound in the second sample using the second of the at least two differing and independent analytical techniques, wherein the at least two differing and independent analytical techniques comprise fluorescence spectroscopy and gas chromatography-mass spectrometry.

Further disclosed herein is a method of increasing agreement between at least two differing and independent analytical techniques, the method comprising: obtaining a first sample comprising (a) a hydrocarbon, (b) a marking compound producing a signal in response to a stimulus, and (c) at least one signal-dampening material, wherein the first sample has a first homogeneity; determining a concentration of the marking compound in the first sample using a first of the at least two differing and independent analytical techniques; contacting a matrix with an aliquot of the first sample in a volumetric ratio of greater than or equal to about 5:1 to produce a second sample, wherein the second sample has a second homogeneity that is greater than the first homogeneity; and determining an amount of the marking compound in the second sample using a second of the at least two differing and independent analytical techniques.

Also disclosed herein is a method of identifying an adulterated fuel composition comprising: obtaining a plurality of fuel samples comprising (i) a hydrocarbon fuel, and (ii) a fluorescent marking compound; obtaining an emission spectra for each of the plurality of fuel samples; identifying, from the emission spectra of each of the plurality of fuel samples, one or more samples (i) lacking a solvatochromic shift and (ii) displaying a decrease in signal intensity for one or more signals present in the emission spectra; for each of the one or more identified samples, contacting a matrix with an aliquot of the sample in a volumetric ratio of greater than or equal to about 5:1 to produce a second sample; determining the amount of fluorescent marking compound present in the identified sample based on the amount of fluorescent marking compound present in the second sample; comparing the amount of fluorescent marking compound present in the identified sample to an amount present in an unadulterated fuel; and classifying the identified sample as comprising unadulterated or adulterated fuel.

Further disclosed herein is a method of identifying an adulterated fuel composition utilizing at least two differing and independent analytical techniques, the method comprising: obtaining a plurality of fuel samples comprising (i) a hydrocarbon fuel and (ii) a fluorescent marking compound; obtaining an emission spectra of each of the plurality of fuel samples; identifying, from the emission spectra of each of the plurality of fuel samples, one or more samples (i) lacking a solvatochromic shift and (ii) displaying a decrease in signal intensity for one or more signals present in the emission spectra; for each of the one or more identified samples, contacting a matrix with an aliquot of the sample in a volumetric ratio of greater than or equal to about 5:1 to produce a second sample; determining the amount of fluorescent marking compound present in the second sample; determining the amount of fluorescent marking compound present in the plurality of fuel samples utilizing a second independent analytical technique; comparing the amount of fluorescent marking compound determined based on the emission spectra of the identified samples with the amount determined based on the second independent analytical technique, wherein a difference in the amount of fluorescent marking compound determined based on the emission spectra and an amount of fluorescent marking compound determined based on the second analytical technique is in the range of from about ±5% to about ±10%; and classifying the identified sample as comprising unadulterated or adulterated fuel, by comparing the amount of fluorescent marking compound in the identified sample to an amount present in unadulterated fuel.

Also disclosed herein is a method of authentication comprising: obtaining from a first site a fuel sample comprising (i) at least one hydrocarbon, (ii) a marking compound and (iii) a homogeneity-varying material wherein the first site is proximal to a fuel storage area; contacting a matrix with a first aliquot of the fuel sample in a volumetric ratio of greater than or equal to about 5:1 to produce a corresponding diluted fuel sample having a dilution factor equivalent to the volumetric ratio of matrix to aliquot of the fuel sample; obtaining the fluorescence emission spectra of the diluted fuel sample; determining an amount of marking compound present in the diluted fuel sample based on the fluorescence emission spectra; determining an amount, referred to as the fluorescence-derived amount, of marking compound present in the fuel sample via application of the dilution factor to the amount of marking compound present in the diluted fuel sample; comparing the fluorescence-derived amount to a threshold value, wherein the threshold value is the expected or standard amount of marking compound present in an unadulterated fuel of the type stored and sampled at the fuel storage area; identifying the fuel sample as a possibly adulterated fuel when the fluorescence-derived amount is less than the threshold value; transferring, to a testing site distal to the storage area, a second aliquot of the fuel sample; at the second site, analyzing the second aliquot of the first sample by gas chromatography-mass spectrometry to determine an amount, referred to as GC/MS-derived amount, of marking compound present in the fuel sample; and comparing the GC/MS-derived amount to a threshold value, wherein the threshold value is the expected or standard amount of marking compound present in an unadulterated fuel of the type stored and sampled at the fuel storage area.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DETAILED DESCRIPTION

Figure 1:
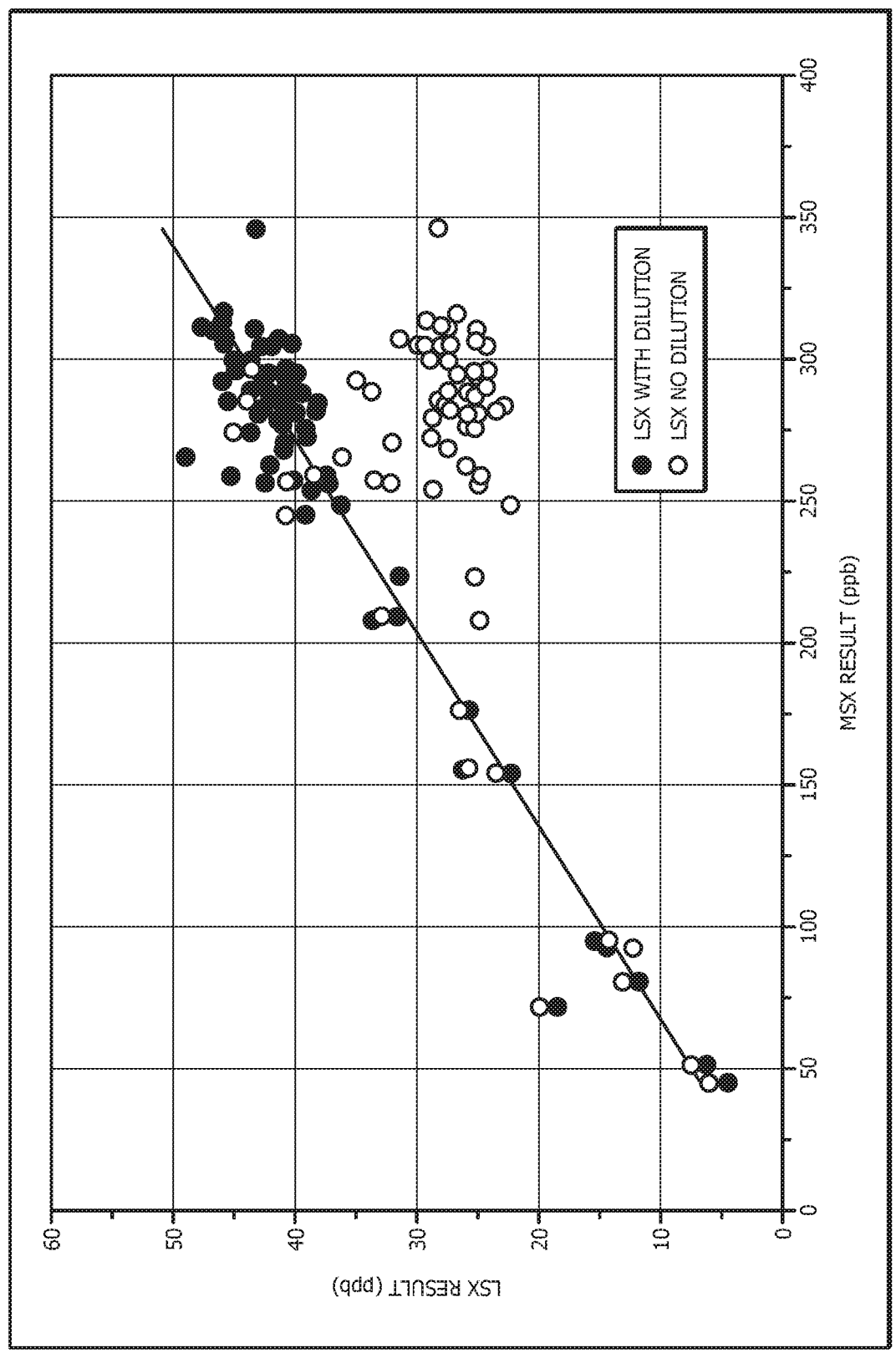
FIG. 1 is a plot of results from gasoline analysis of Example 1.

It should be understood at the outset that although an illustrative implementation of one or more embodiments is provided below, the disclosed systems, methods, and/or products may be implemented using any number of techniques, whether currently known or in existence. The disclosure should in no way be limited to the illustrative implementations, drawings, and techniques illustrated hereinbelow, including the exemplary designs and implementations illustrated and described herein, but may be modified within the scope of the appended claims along with their full scope of equivalents.

As noted above, herein disclosed is a method of increasing accuracy of the quantification of an analyte in a hydrocarbon. In embodiments, the method provides for increasing agreement between at least two differing and independent analytical techniques. Such a method may be particularly suitable when marking compounds have variable response (i.e., intensity) without substantial changes to analytical measurements, such as without limitation spectral shape and/or wavelength, due to varying fuel composition, and/or the presence of homogeneity-varying or signal-dampening materials therein.

In embodiments, a method of increasing accuracy of the quantification of an analyte in a hydrocarbon according to this disclosure comprises obtaining a first sample comprising (a) the hydrocarbon and (b) an analyte comprising a marking compound; obtaining a homogeneity inducing material (also referred to herein as a "matrix" or "solvent"); contacting the homogeneity inducing material with an aliquot of the first sample in a desired volumetric ratio of the homogeneity inducing material to the first sample (e.g., a volumetric ratio of greater than or equal to about 7:1) to produce a second sample; and determining an amount of the marking compound in the second sample using an analytical technique based on the marking material.

In embodiments, the method comprises obtaining a first sample, wherein the first sample has a first degree of homogeneity; contacting an aliquot of the first sample with a matrix to produce a second sample, wherein the second sample has a second degree of homogeneity that is greater than the first degree of homogeneity; and determining an amount of the marking compound in the second sample using a first of the at least two differing and independent analytical techniques. In an embodiment, the method further comprises determining an amount of the marking compound in the first sample using a second of the at least two differing techniques. In some embodiments, the method comprises determining an amount of the marking compound in the second sample using both the first and the second of the at least two differing techniques.

Determination of the amount of marking compound based on the results obtained by subjecting a sample (e.g., first or second) to the differing analytical technique(s) may be based on any suitable methodology consistent with the applied technique. For example, when utilizing a technique that involves a spectroscopic signal for the marking compound of interest relevant parameters (e.g., extinction coefficient, absorption/emission maxima, etc.) may be used to determine the sample concentration of marking compound. Alternative suitable methodologies for determination of the amount of marking compound present in a sample may include the preparation of a calibration curve using standards of known concentration which is subsequently utilized to calculate the amount of sample having an unknown concentration.

The (first) sample can comprise a hydrocarbon, a marking compound, and a homogeneity-varying material. In embodiments, the hydrocarbon comprises a fuel. In embodiments, the hydrocarbon comprises gasoline, diesel fuel, biodiesel fuel, kerosene, liquefied petroleum gas, ethanol, or a combination thereof. The hydrocarbon or fuel can further comprise one or more components typically found therein, such as, without limitation, oxygenates, antioxidants, antiknock agents, lead scavengers, corrosion inhibitors, viscosity modifiers, pour point depressants, friction modifiers, anti-wear additives, dispersants, antioxidants, metal deactivators, and combinations thereof.

The marking compound can be any marking compound known to those of skill in the art to produce a signal in response to a stimulus. In embodiments, the marking compound comprises a fluorescent marking compound. In embodiments, the marking compound comprises an organic compound having a fluorescence in the wavelength range of from about 450 nm to about 650 nm, from about 525 nm to about 725 nm, or from about 600 nm to about 800 nm. In embodiments, the marking compound comprises a phthalocyanine, a violanthrone, an azadipyrromethene, naphthalocyanine, rhodamine, oxazine, coumarin, a cyanine fluorophore, or a combination thereof.

When a fluorescence molecule is moved from the gas phase into a solvent, a solvent-specific alteration of its optical properties results. Similar changes in the optical properties of a fluorophore are also expected when the solvent used to solvate the fluorophore is changed; these stem from each solvent possessing unique structural and electronic properties that interact differently with both the ground and excited states of the fluorophore. This change of optical transition energies of the fluorescent molecule is termed solvatochromic shifting. In embodiments, the marking compound is not resistant to solvatochromic shifting. In embodiments, the marking compound is resistant to solvatochromic shifting. In embodiments, the marking compound is present in an amount of from about 0.1 ppb to about 1,000 ppb, from about 0.5 ppb to about 500 ppb, or from about 1 ppb to about 100 ppb.

The homogeneity-varying material is also referred to herein as a 'signal-dampening material'. In embodiments, the homogeneity-varying material or 'signal-dampening material' comprises one or more other refined fuel products, biofuels, fuel additives, oxygenates, common fuel adulterants, or a combination thereof. The homogeneity-varying material in the fuel may result from naturally occurring variances in the fuel, and/or from adulteration of the fuel with components prior to the addition of the markers. In embodiments, the signal—dampening material or homogeneity varying material is present in the fuel in an amount of from about 1 ppm to about 10 weight percent, from about 5 ppm to about 5 weight percent, or from about 10 ppm to about 1 weight percent. In embodiments, the signal—dampening material or homogeneity varying material reduces a signal intensity (e.g., a fluorescence signal intensity) of a marking compound (e.g., of a fluorescent marking compound) by an amount in the range of from about 1% to about 100%, from about 1% to about 95%, or from about 1% to about 90%.

Via addition of the matrix or homogeneity inducing material, the homogeneity of the sample is increased. For example, in embodiments, a first or 'non-matrix-regulated' sample has a first degree of homogeneity in the range of from about 0.1 to about 0.4, from about 0.1 to about 0.3, or from about 0.1 to about 0.2. The "degree of homogeneity" herein refers to a scale of 0 to 1 wherein a pure sample comprising a solvated known compound is designated to have a degree of homogeneity of 1 while a sample comprising a plurality of compounds (e.g., greater than about 5) wherein at least one of the compounds is unknown is designated as having a degree of homogeneity of 0. In embodiments, the first sample has a first homogeneity that is less than or equal to about 0.5, 0.4, 0.3, 0.2, or 0.1. In embodiments, the second or 'matrix-regulated' sample has a second degree of homogeneity in the range of from about 0.5 to about 1.0, from about 0.7 to about 0.95, or from about 0.8 to about 0.95. In embodiments, the second sample has a second homogeneity that is greater than or equal to about 0.5, 0.6, 0.7, 0.8, 0.9, or 0.95.

Without wishing to be limited by theory, the addition of the matrix may mitigate changes in fluorescence due to solvent effects by normalizing the solvent environment around the fluorophore by addition of consistent solvent to the sample. This approach may help to minimize solvatochromic shifting in the fluorescence spectrum by ensuring that the fluorophore is always surrounded by the solvent molecules in solution, and hence provides a consistent fluorescence spectrum. This approach can significantly improve quantitation results when fluorophores are present in varying solvents, providing the dilution is not so large as to approach the detection limits of the instrument being utilized to make the measurement.

In embodiments, the matrix comprises, consists, or consists essentially of one or more aliphatic hydrocarbons, aromatic hydrocarbons, petroleum distillates, halogenated aliphatic hydrocarbons, halogenated aromatic hydrocarbons, or a combination thereof. In embodiments, the matrix comprises, consists, or consists essentially of mesitylene (1,3,5-trimethylbenzene). In embodiments, the matrix is added to provide a desired volumetric ratio of the matrix to the first sample (e.g., aliquot comprising the hydrocarbon or fuel). For example, the desired volumetric ratio may be greater than or equal to about 2:1, 3:1, 4:1, 5:1, 6:1, 7:1, 8:1, 9:1, or 10:1. In embodiments, the matrix is added such that the ratio of the matrix to the first sample (e.g., aliquot comprising the hydrocarbon or fuel) is in the range of from about 1:1 to about 15:1, from about 5:1 to about 10:1, or from about 7:1 to about 8:1. Matrix addition may provide a balance mitigating the solvent effect (where higher ratios may be better) and the loss of signal for detectability (where lower ratios may be better).

The analytical technique(s) can comprise, without limitation, fluorescence spectroscopy, gas chromatography (GC), mass spectrometry (MS), ultraviolet spectroscopy, high-pressure liquid chromatography (HPLC), infrared spectroscopy, or a combination thereof. In embodiments, the method further comprises determining an amount of the marking compound in the first sample using the at least two differing and independent analytical techniques. In embodiments, the at least two differing and independent analytical techniques comprise fluorescence spectroscopy and gas chromatography-mass spectrometry (GC/MS). In embodiments, the agreement between the at least two differing and independent analytical techniques is increased by equal to or greater than about 5%, 6%, 7%, 8%, 9%, or 10% via the disclosed method, based on the percentage difference in values obtained from a corresponding (e.g., like or identical) sample in the absence of the matrix. In embodiments, the agreement between the at least two differing and independent analytical techniques is increased by equal to or greater than about 5%, 6%, 7%, 8%, 9%, or 10% via the disclosed method, based on the percentage difference in values obtained from testing matrix-regulated and non-matrix-regulated samples of the same fuel.

In embodiments, the concentration of marking compound in a non-matrix regulated sample is determined using a first analytical technique is determined. In such embodiments, the concentration of marking compound in a matrix regulated sample using a second analytical technique is determined. The percentage difference between the concentration of marking compound determined for the non-matrix regulated sample and the matrix-regulated sample may be in the range of from about ±5% to about ±10%. In embodiments, the percentage difference is less than or equal to about 10%, 9%, 8%, 7%, 6%, or 5%.

In embodiments, the method further comprises determining an amount of the marking compound (e.g., the fluorescent marking compound) in the hydrocarbon/fuel. For example, in embodiments, the method further comprises determining, based on the amount of marking compound present in the matrix-containing (e.g., the second) sample, an amount of marking compound present in the hydrocarbon or first, non-matrix regulated sample as will be described in more detail later herein.

The herein-disclosed method may be operable to identify an adulterated fuel. For example, a method of identifying an adulterated fuel composition according to an embodiment of this disclosure comprises obtaining a plurality of fuel samples comprising a hydrocarbon fuel, and a fluorescent marking compound; obtaining an emission spectra for each of the plurality of fuel samples; identifying, from the emission spectra of each of the plurality of fuel samples, one or more samples lacking a solvatochromic shift and displaying a decrease in signal intensity for one or more signals present in the emission spectra; for each of the one or more identified samples, contacting an aliquot of the sample with a matrix, as described hereinabove, to produce a second sample; determining the amount of fluorescent marking compound present in the identified sample based on the amount of fluorescent marking compound present in the second sample; comparing the amount of fluorescent marking compound present in the identified sample to an amount present in an unadulterated fuel; and classifying the identified sample as comprising unadulterated or adulterated fuel. In embodiments, the matrix is added such that the ratio of the fuel sample to the matrix is less than or equal to about 1:5, 1:6, 1:7, 1:8, 1:9, or 1:10. The ratio of fuel sample to the matrix is also termed the dilution factor.

In embodiments, a method of identifying an adulterated fuel composition according to an embodiment of this disclosure comprises identifying an adulterated fuel composition utilizing at least two differing and independent analytical techniques by obtaining a plurality of fuel samples comprising a hydrocarbon fuel and a fluorescent marking compound; obtaining an emission spectra of each of the plurality of fuel samples; identifying, from the emission spectra of each of the plurality of fuel samples, one or more samples lacking a solvatochromic shift and displaying a decrease in signal intensity for one or more signals present in the emission spectra; for each of the one or more identified samples, contacting an aliquot of the sample with a matrix as described hereinabove to produce a second sample; determining the amount of fluorescent marking compound present in the second sample; determining the amount of fluorescent marking compound present in the plurality of fuel samples utilizing a second independent analytical technique; comparing the amount of fluorescent marking compound determined based on the emission spectra of the identified samples with the amount determined based on the second independent analytical technique, wherein a difference in the amount of fluorescent marking compound determined based on the emission spectra and an amount of fluorescent marking compound determined based on the second analytical technique is within a desired range, and classifying the identified sample as comprising unadulterated or adulterated fuel, by comparing the amount of fluorescent marking compound in the identified sample to an amount present in unadulterated fuel. In embodiments, the matrix is added such that the volumetric ratio of the fuel sample to the matrix is less than or equal to about 1:7, 1:8, 1:9, or 1:10. In embodiments, the difference in the amount of fluorescent marking compound determined based on the emission spectra and the amount of fluorescent marking compound determined based on the second analytical technique is in the range of from about ±1% to about ±15%, from about ±5% to about ±15%, or from about ±5% to about ±10%. In embodiments, the difference in the amount of fluorescent marking compound determined based on the emission spectra and the amount of fluorescent marking compound determined based on the second analytical technique is less than or equal to about 10%, 9%, 8%, 7%, 6%, or 5%.

As noted hereinabove, the herein-disclosed method enables improved accuracy in quantifying marking compounds, such as fluorescent marking compounds, in hydrocarbons, such as fuels. The addition of a suitable amount of the herein-disclosed matrix according to this disclosure can increase agreement between at least two differing and independent analytical techniques. For example, the disclosed method can be utilized to improve the agreement in measurement of marking compound concentrations obtained via fluorescence spectroscopy and GC/MS, in embodiments. In embodiments, the method can increase the agreement in the measurement of marking compound concentrations obtained via the two differing and independent techniques, such that the concentrations of the marker compound determined thereby are within about 15% or less. Such methods may be particularly suitable in instances wherein the hydrocarbon or fuel containing the marker comprises significant amounts of signal-dampening or homogeneity-varying material which interact with (e.g., reduce a signal intensity produced via the marking compound) the readings obtained via the analytical techniques.

EXAMPLE

The embodiments having been generally described, the following example is given as a particular embodiment of the disclosure and to demonstrate the practice and advantages thereof. It is understood that the example is given by way of illustration and is not intended to limit the specification or the claims in any manner.

Example 1: Enhanced Correlation of LSX and MSX Marker Results in Fuels Via Matrix Regulation A laboratory-based study on more than 100 fuel samples collected from the field was conducted looking for methodology to improve the consistency between results obtained using LSX and MSX markers. LSX and MSX both refer to device platforms commercially available from Authentix. LSX employs laser-induced fluorescence spectroscopy to measure marking compounds in a variety of liquids while MSX employs gas chromatography-mass spectrometry.

In this experiment, the efficacy of employing a matrix regulation (i.e., solvent dilution) strategy was evaluated on over 100 samples from the field that were deemed problematic using conventional analysis protocols. Since all of the samples in the study were from the field, the actual concentrations of both the LSX and MSX markers were not known with any degree of certainty, and thus conventional accuracy statistics could not be utilized. However, what was known with certainty was that there should be a linear correlation between the MSX and LSX marker results since both markers are dosed via a single concentrate. Therefore, to determine the efficacy of the matrix regulation method of this disclosure, linear correlation coefficients were determined for the samples using both the conventional analysis protocols (e.g., direct analysis of the fuels on the LSX 2000), and the matrix addition method described herein.

The conventional analysis comprised fluorescence spectroscopy without sample dilution. Via conventional analysis, the unknown sample is transferred directly into the analysis vial. Upon excitation via laser (632 nm) the fluorescent light emitted from the sample is collected on a linear silicon CCD array based spectrometer. The spectrum is processed via a multivariate model to estimate the concentration of marker in the sample.

Chemicals and Reagents.

Fuel samples, 66 gasoline and 36 diesel, were obtained from the field. Mesitylene (Acros Organics, 99.0%, extra pure) was obtained from Fisher Scientific and used without further purification.

GC/MS analyses were performed on an Agilent 5975T gas chromatograph/mass selective detector using the methodology outlined in U.S. Pat. No. 9,366,661, the disclosure of which is hereby incorporated herein in its entirety for all purposes not contrary to this disclosure.

For sample analysis, 0.750 mL of the fuel sample was added to a LSX vial via a BrandTech Transferpettor Positive Displacement Pipette (200-1000 μL). To this was added 4.75 mL of mesitylene via a Fortuna Optifix Bottle Top Dispenser (1-5 mL, Solvent model). The sample was then inverted several times to ensure mixing prior to analysis on the LSX 2000.

LSX Quantitation.

For dilution analyses, it is necessary to correct for the dilution of the sample prior to reporting the quantitative result. This is accomplished simply by multiplying the LSX calculated result by the dilution factor (DF) used for the dilution (i.e., the ratio of the amount of matrix added to the sample), in the present work the DF was 7.33.

As noted hereinabove, a strong correlation between the analytical results provided by the MSX and the LSX was expected since both markers are added via a single concentrate solution during marking operations. When adulteration of the fuel occurs, both markers will be diluted by the same amount, meaning a linear correlation between the two is expected, and the correlation curve should fit through zero. Coefficients of determination ($R^2$) obtained with and without matrix regulation are shown in Table 1 hereinbelow.

TABLE 1

Correlation Coefficients for MSX and LSX Results for Gasoline and Diesel Samples in Example 1

| Fuel Type | Coefficient of determination ($R^2$) |
|---|---|
| Gasoline: | |
| LSX with Matrix Regulation | 0.9141 |
| LSX without Matrix Regulation | 0.1924 |
| Diesel: | |
| LSX with Matrix Regulation | 0.8963 |
| LSX without Matrix Regulation | 0.8552 |

Figure 2:
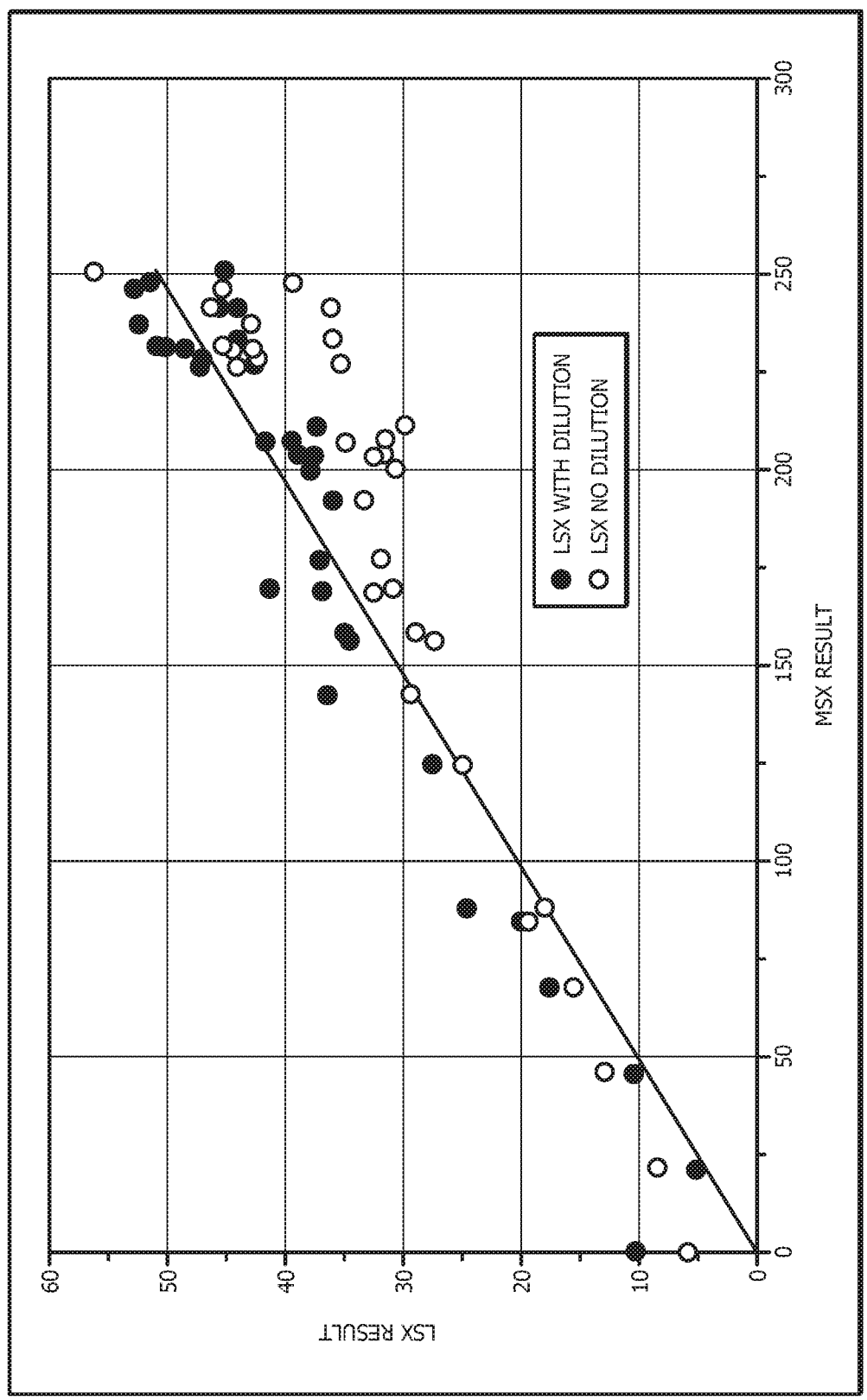
FIG. 2 is a plot of results from diesel analysis of Example 1.

FIG. 1 is a plot of the results obtained from the gasoline analysis in this Example. FIG. 2 is a plot of the results obtained from the diesel analysis in this Example. The samples were analyzed directly via LSX using non-matrix regulation protocols, and then analyzed after matrix regulation with mesitylene. In FIGS. 1 and 2, both datasets (i.e., LSX results with and without matrix regulation) are plotted against the MSX results of the same samples.

As seen in Table 1, and the Figures, for both gasoline and diesel samples, an improvement in the correlation of determination ($R^2$) was observed after matrix regulation of the samples via the addition of mesitylene. In the case of gasoline, a dramatic improvement was observed, with the $R^2$ improving from 0.1924 to 0.9141 after regulating the matrix of the samples with mesitylene.

The herein-disclosed matrix regulation method thus, under these laboratory conditions, improved the correlation between MSX and LSX results in problematic fuel samples from the field. Without wishing to be limited by theory, combining the fuel samples with mesitylene, according to the method of this disclosure, homogenized the solvent environment around the fluorophore. In theory, this may serve to correct for inconsistencies in the fuel matrices based on the variable composition of different fuels and/or minimize the impact of quantitation when specific problematic fuel adulterants are utilized to dilute fuels. The results of Example 1 demonstrate improvement in the correlation of MSX to LSX results, particularly notable in gasoline samples, for which the $R^2$ for the correlation increased from 0.1924 to 0.9141. Accurately matrix regulation of the fuel samples with mesitylene, according to the method of this disclosure, thus dramatically improved the correlation of LSX and MSX results, in particular for problematic gasoline samples.

While various embodiments have been shown and described, modifications thereof can be made by one skilled in the art without departing from the spirit and teachings of the disclosure. The embodiments described herein are exemplary only, and are not intended to be limiting. Many variations and modifications of the subject matter disclosed herein are possible and are within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_L$ and an upper limit, $R_U$ is disclosed, any number falling within the range is specifically disclosed. In particular, the following numbers within the range are specifically disclosed: $R=R_L+k*(R_U-R_L)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the embodiments of the present disclosure. The discussion of a reference is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural, or other details supplementary to those set forth herein.

Additional Description

The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Alternative embodiments that result from combining, integrating, and/or omitting features of the embodiment(s) are also within the scope of the disclosure. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

Embodiments disclosed herein include:

A: A method of increasing accuracy of the quantification of an analyte in a hydrocarbon, the analyte comprising a marking compound, the method comprising: obtaining a first sample comprising (a) the hydrocarbon and (b) the marking compound; obtaining a homogeneity inducing material; contacting the homogeneity inducing material with an aliquot of the first sample in a volumetric ratio of greater than or equal to about 5:1 to produce a second sample; and determining an amount of the marking compound in the second sample using an analytical technique based on the marking material.

B: A method of increasing agreement between at least two differing and independent analytical techniques, the method comprising: obtaining a first sample comprising (a) a hydrocarbon, (b) a marking compound, and (c) a homogeneity-varying material, wherein the first sample has a degree of homogeneity in the range of from about 0.1 to about 0.4; contacting a matrix with an aliquot of the first sample in a volumetric ratio of greater than or equal to about 5:1 to produce a second sample, wherein the second sample has a degree of homogeneity in the range of from about 0.8 to about 0.95; determining an amount of the marking compound in the first sample using a first of the least two differing and independent analytical techniques; and determining an amount of the marking compound in the second sample using a second of the least two differing and independent analytical techniques.

C: A method of increasing agreement between at least two differing and independent analytical techniques, the method comprising: obtaining a fuel comprising (a) a fluorescent marking compound and (b) a signal-dampening material, wherein the fuel has a degree of homogeneity in the range of from about 0.1 to about 0.2; contacting a matrix with an aliquot of the fuel in a volumetric ratio of greater than or equal to about 5:1 to produce a sample, wherein the sample has a degree of homogeneity of greater than or equal to about 0.8; and determining a concentration of the fluorescent marking compound in the sample using a first of the at least two differing and independent analytical techniques.

D: A method of increasing agreement between at least two differing and independent analytical techniques, the method comprising: obtaining a first sample comprising (a) a hydrocarbon, (b) a marking compound producing a signal in response to a stimulus, and (c) at least one signal-dampening material; determining an amount of the marking compound in the first sample using a first of the at least two differing and independent analytical techniques; contacting a matrix with an aliquot of the first sample in a volumetric ratio of greater than or equal to about 5:1 to produce a second sample; and determining an amount of the marking compound in the second sample using the second of the at least two differing and independent analytical techniques, wherein the at least two differing and independent analytical techniques comprise fluorescence spectroscopy and gas chromatography-mass spectrometry.

E: A method of increasing agreement between at least two differing and independent analytical techniques, the method comprising: obtaining a first sample comprising (a) a hydrocarbon, (b) a marking compound producing a signal in response to a stimulus, and (c) at least one signal-dampening material, wherein the first sample has a first homogeneity; determining a concentration of the marking compound in the first sample using a first of the at least two differing and independent analytical techniques; contacting a matrix with an aliquot of the first sample in a volumetric ratio of greater than or equal to about 5:1 to produce a second sample, wherein the second sample has a second homogeneity that is greater than the first homogeneity; and determining an amount of the marking compound in the second sample using a second of the at least two differing and independent analytical techniques.

F: A method of identifying an adulterated fuel composition comprising: obtaining a plurality of fuel samples comprising (i) a hydrocarbon fuel, and (ii) a fluorescent marking compound; obtaining an emission spectra for each of the plurality of fuel samples; identifying, from the emission spectra of each of the plurality of fuel samples, one or more samples (i) lacking a solvatochromic shift and (ii) displaying a decrease in signal intensity for one or more signals present in the emission spectra; for each of the one or more identified samples, contacting a matrix with an aliquot of the sample in a volumetric ratio of greater than or equal to about 5:1 to produce a second sample; determining the amount of fluorescent marking compound present in the identified sample based on the amount of fluorescent marking compound present in the second sample; comparing the amount of fluorescent marking compound present in the identified sample to an amount present in an unadulterated fuel; and classifying the identified sample as comprising unadulterated or adulterated fuel.

G: A method of identifying an adulterated fuel composition utilizing at least two differing and independent analytical techniques, the method comprising: obtaining a plurality of fuel samples comprising (i) a hydrocarbon fuel and (ii) a fluorescent marking compound; obtaining an emission spectra of each of the plurality of fuel samples; identifying, from the emission spectra of each of the plurality of fuel samples, one or more samples (i) lacking a solvatochromic shift and (ii) displaying a decrease in signal intensity for one or more signals present in the emission spectra; for each of the one or more identified samples, contacting a matrix with an aliquot of the sample in a volumetric ratio of greater than or equal to about 5:1 to produce a second sample; determining the amount of fluorescent marking compound present in the second sample; determining the amount of fluorescent marking compound present in the plurality of fuel samples utilizing a second independent analytical technique; comparing the amount of fluorescent marking compound determined based on the emission spectra of the identified samples with the amount determined based on the second independent analytical technique, wherein a difference in the amount of fluorescent marking compound determined based on the emission spectra and an amount of fluorescent marking compound determined based on the second analytical technique is in the range of from about ±5% to about ±10%; and classifying the identified sample as comprising unadulterated or adulterated fuel, by comparing the amount of fluorescent marking compound in the identified sample to an amount present in unadulterated fuel.

H: A method of authentication comprising: obtaining from a first site a fuel sample comprising (i) at least one hydrocarbon, (ii) a marking compound and (iii) a homogeneity-varying material wherein the first site is proximal to a fuel storage area; contacting a matrix with a first aliquot of the fuel sample in a volumetric ratio of greater than or equal to about 5:1 to produce a corresponding diluted fuel sample having a dilution factor equivalent to the volumetric ratio of matrix to aliquot of the fuel sample; obtaining the fluorescence emission spectra of the diluted fuel sample; determining an amount of marking compound present in the diluted fuel sample based on the fluorescence emission spectra; determining an amount, referred to as the fluorescence-derived amount, of marking compound present in the fuel sample via application of the dilution factor to the amount of marking compound present in the diluted fuel sample; comparing the fluorescence-derived amount to a threshold value, wherein the threshold value is the expected or standard amount of marking compound present in an unadulterated fuel of the type stored and sampled at the fuel storage area; identifying the fuel sample as a possibly adulterated fuel when the fluorescence-derived amount is less than the threshold value; transferring, to a testing site distal to the storage area, a second aliquot of the fuel sample; at the second site, analyzing the second aliquot of the first sample by gas chromatography-mass spectrometry to determine an amount, referred to as GC/MS-derived amount, of marking compound present in the fuel sample; and comparing the GC/MS-derived amount to a threshold value, wherein the threshold value is the expected or standard amount of marking compound present in an unadulterated fuel of the type stored and sampled at the fuel storage area.

Each of embodiments A, B, C, D, E, F, G and H may have one or more of the following additional elements: Element 1: further comprising determining whether the first sample is adulterated based on a comparison of the amount of the marking compound in the first sample to a reference standard having a known amount of the marking compound. Element 2: wherein the analytical technique(s) comprises fluorescence spectroscopy, gas chromatography, mass spectrometry, ultraviolet spectroscopy, high-pressure liquid chromatography, infrared spectroscopy, or a combination thereof. Element 3: wherein the hydrocarbon comprises gasoline, diesel fuel, biodiesel fuel, kerosene, liquefied petroleum gas, ethanol, or a combination thereof. Element 4: wherein the marking compound comprises an organic compound having a fluorescence in the wavelength range of from about 600 nm to about 800 nm. Element 5: wherein the marking compound comprises a phthalocyanine, a violanthrone, an azadipyrromethene, naphthalocyanine, rhodamine, oxazine, coumarin, a cyanine fluorophore, or a combination thereof. Element 6: wherein the marking compound is not resistant to solvatochromic shifting. Element 7: wherein the marking compound is present in an amount of from about 1 ppb to about 1000 ppb. Element 8: wherein the homogeneity inducing material comprises one or more aliphatic hydrocarbons, aromatic hydrocarbons, petroleum distillates, halogenated aliphatic hydrocarbons, halogenated aromatic hydrocarbons, or a combination thereof. Element 9: the matrix comprises one or more aliphatic hydrocarbons, aromatic hydrocarbons, petroleum distillates, halogenated aliphatic hydrocarbons, halogenated aromatic hydrocarbons, or a combination thereof. Element 10: wherein the homogeneity-varying material comprises one or more other refined fuel products, biofuels, fuel additives, oxygenates, common fuel adulterants, or a combination thereof. Element 11: wherein the agreement between the at least two differing and independent analytical techniques is increased by at least 5%, based on the percentage difference in values obtained in the absence of the matrix. Element 12: wherein the at least two differing and independent analytical techniques comprise fluorescence spectroscopy and gas chromatography-mass spectrometry. Element 13: further comprising determining an amount of the fluorescent marking compound in the fuel. Element 14: further comprising determining whether the fuel is adulterated based on a comparison of the amount of the fluorescent marking compound in the fuel to a reference standard having a known amount of the marking compound. Element 15: wherein the fuel comprises gasoline, diesel fuel, biodiesel fuel, kerosene, liquefied petroleum gas, ethanol, or a combination thereof. Element 16: wherein the fluorescent marking compound has a fluorescence in the wavelength range of from about 600 nm to about 800 nm. Element 17: wherein the fluorescent marking compound comprises a phthalocyanine, a violanthrone, an azadipyrromethene, naphthalocyanine, rhodamine, oxazine, coumarin, a cyanine fluorophore, or a combination thereof. Element 18: wherein the fluorescent marking compound is not resistant to solvatochromic shifting. Element 19: wherein the fuel further comprises one or more oxygenates, antioxidants, antiknock agents, lead scavengers, corrosion inhibitors, viscosity modifiers, pour point depressants, friction modifiers, antiwear additives, dispersants, antioxidants, metal deactivators, or a combination thereof. Element 20: wherein the signal—dampening material is present in the fuel in an amount of from about 1 ppm to about 10 weight percent. Element 21: wherein the signal—dampening material reduces from about 1% to about 90% of a fluorescence signal intensity of the fluorescent marking compound. Element 22: further comprising determining a percentage difference between the amount of marking compound determined using the first and the second of the at least two differing and independent analytical techniques. Element 23: wherein the percentage difference is in the range of from about ±5% to about ±10%. Element 24: further comprising determining, based on the amount of marking compound present in the second sample, an amount of marking compound present in the first sample. Element 25: further comprising determining, based on the amount of marking compound present in the second sample, an amount of marking compound present in the first sample; and determining whether the first sample is adulterated based on a comparison of the amount of the marking compound in the first sample to a reference standard having a known amount of the marking compound. Element 26: further comprising identifying the fuel as adulterated when the GC/MS-derived amount is less than the threshold value. Element 27: further comprising: comparing the fluorescence-derived amount to the GC/MS-derived amount to determine a difference, and identifying the fuel sampled at the fuel storage area as adulterated when the difference is <=±5%. Element 28: wherein the contacting of the matrix or homogeneity inducing material with the aliquot of the first sample to produce the second sample is in a volumetric ratio of greater than or equal to about 7:1.

While preferred embodiments of the invention have been shown and described, modifications thereof can be made by one skilled in the art without departing from the teachings of this disclosure. The embodiments described herein are exemplary only, and are not intended to be limiting. Many variations and modifications of the invention disclosed herein are possible and are within the scope of the invention.

Numerous other modifications, equivalents, and alternatives, will become apparent to those skilled in the art once the above disclosure is fully appreciated. It is intended that the following claims be interpreted to embrace all such modifications, equivalents, and alternatives where applicable. Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A method of quantification of an analyte in a hydrocarbon, the analyte comprising a marking compound, the method comprising:
    obtaining a first sample comprising (a) the hydrocarbon and (b) the marking compound;
    obtaining a homogeneity inducing material operable to increase the homogeneity of the first sample;
    contacting the homogeneity inducing material with an aliquot of the first sample in a volumetric ratio of greater than or equal to about 5:1 to produce a second sample; and
    determining an amount of the marking compound in the second sample using an analytical technique.

2. The method of claim 1 further comprising determining whether the first sample is adulterated based on a comparison of an amount of the marking compound in the first sample to a reference standard having a known amount of the marking compound.

3. The method of claim 1, wherein the analytical technique comprises fluorescence spectroscopy, gas chromatography, mass spectrometry, ultraviolet spectroscopy, high-pressure liquid chromatography, infrared spectroscopy, or a combination thereof.

4. The method of claim 1, wherein the hydrocarbon comprises gasoline, diesel fuel, biodiesel fuel, kerosene, liquefied petroleum gas, ethanol, or a combination thereof.

5. The method of claim 1, wherein the marking compound comprises an organic compound having a fluorescence in a wavelength range of from about 600 nm to about 800 nm.

6. The method of claim 5, wherein the marking compound comprises a phthalocyanine, a violanthrone, an azadipyrromethene, naphthalocyanine, rhodamine, oxazine, coumarin, a cyanine fluorophore, or a combination thereof.

7. The method of claim 1, wherein the marking compound is not resistant to solvatochromic shifting.

8. The method of claim 1, wherein the marking compound is present in an amount of from about 1 ppb to about 1000 ppb.

9. The method of claim 1, wherein the homogeneity inducing material comprises one or more aliphatic hydrocarbons, aromatic hydrocarbons, petroleum distillates, halogenated aliphatic hydrocarbons, halogenated aromatic hydrocarbons, or a combination thereof.

10. The method of claim 1 further comprising determining whether the first sample is adulterated based on a comparison of an amount of the marking compound in the first sample to a reference standard having a known amount of the marking compound;
    wherein the analytical technique comprises fluorescence spectroscopy, gas chromatography, mass spectrometry, ultraviolet spectroscopy, high-pressure liquid chromatography, infrared spectroscopy, or a combination thereof; and
    wherein the hydrocarbon comprises gasoline, diesel fuel, biodiesel fuel, kerosene, liquefied petroleum gas, ethanol, or a combination thereof.

11. The method of claim 10, wherein the marking compound (i) comprises an organic compound having a fluorescence in a wavelength range of from about 600 nm to about 800 nm, (ii) comprises a phthalocyanine, a violanthrone, an azadipyrromethene, naphthalocyanine, rhodamine, oxazine, coumarin, a cyanine fluorophore, or a combination thereof, or (iii) is not resistant to solvatochromic shifting; and
    wherein the homogeneity inducing material comprises one or more aliphatic hydrocarbons, aromatic hydrocarbons, petroleum distillates, halogenated aliphatic hydrocarbons, halogenated aromatic hydrocarbons, or a combination thereof.

12. A method comprising:
    obtaining a first sample comprising (a) a hydrocarbon, (b) a marking compound, and (c) a homogeneity-varying material that reduces a signal intensity of the marking compound measured by a first of at least two differing and independent analytical techniques, wherein the first sample has a degree of homogeneity in a range of from about 0.1 to about 0.4;
    contacting a matrix comprising one or more aliphatic hydrocarbons, aromatic hydrocarbons petroleum distillates, halogenated aliphatic hydrocarbons, halogenated aromatic hydrocarbons, or a combination thereof with an aliquot of the first sample in a volumetric ratio of greater than or equal to about 5:1 to produce a second sample, wherein the second sample has a degree of homogeneity in a range of from about 0.8 to about 0.95;

determining an amount of the marking compound in the first sample using a first of the least two differing and independent analytical techniques; and determining an amount of the marking compound in the second sample using a second of the least two differing and independent analytical techniques, wherein an agreement between amount of the marking compound determined by the first of the at least two differing and independent analytical techniques and the amount of the marking compound determined by the second of the at least two differing and independent analytical techniques is increased relative to a same method absent the matrix.

13. The method of claim 12, wherein the homogeneity-varying material comprises one or more refined fuel products, biofuels, fuel additives, oxygenates, common fuel adulterants, or a combination thereof.

14. The method of claim 12 further comprising determining whether the first sample is adulterated based on a comparison of an amount of the marking compound in the first sample to a reference standard having a known amount of the marking compound.

15. The method of claim 12, wherein the agreement between the at least two differing and independent analytical techniques is increased by at least 5%, relative to a same method absent the matrix.

16. A method comprising:

A obtaining a fuel comprising (a) a fluorescent marking compound and (b) a signal-dampening material which reduces readings obtained via a first of at least two differing and independent analytical techniques, wherein the fuel has a degree of homogeneity in a range of from about 0.1 to about 0.2;

contacting a matrix comprising one or more aliphatic hydrocarbons, aromatic hydrocarbons, petroleum distillates, halogenated aliphatic hydrocarbons, halogenated aromatic hydrocarbons, or a combination thereof with an aliquot of the fuel in a volumetric ratio of greater than or equal to about 5:1 to produce a sample, wherein the sample has a degree of homogeneity of greater than or equal to about 0.8;

determining an amount of the fluorescent marking compound in the sample using the first of the at least two differing and independent analytical techniques; and determining an amount of the fluorescent marking compound in another aliquot of the fuel using a second of the least two differing and independent analytical techniques, wherein an agreement between the amount of the fluorescent marking compound determined by the first of the at least two differing and independent analytical techniques and the amount of the fluorescent marking compound determined by the second of the at least two differing and independent analytical techniques is increased relative to a same method absent the matrix.

17. The method of claim 16, wherein the at least two differing and independent analytical techniques comprise fluorescence spectroscopy and gas chromatography-mass spectrometry.

18. The method of claim 16 further comprising determining an amount of the fluorescent marking compound in the fuel from the amount of the fluorescent marking compound determined by the first of the at least two differing and independent analytical techniques.

19. The method of claim 18 further comprising determining whether the fuel is adulterated based on a comparison of the amount of the fluorescent marking compound in the fuel to a reference standard having a known amount of the marking compound.

20. The method of claim 16, wherein the agreement between the amount of the fluorescent marking compound determined by the first of the at least two differing and independent analytical techniques and the amount of the fluorescent marking compound determined by the second of the at least two differing and independent analytical techniques is increased by at least about 5%, relative to a same method absent the matrix.

* * * * *